(12) United States Patent
Krüger et al.

(10) Patent No.: US 9,615,743 B2
(45) Date of Patent: Apr. 11, 2017

(54) METHOD FOR GENERATING AN ALARM DURING THE MONITORING OF A PATIENT AND DEVICE THEREFOR

(71) Applicant: Drägerwerk AG & Co. KGaA, Lübeck (DE)

(72) Inventors: Thomas Krüger, Reinfeld (DE); Frank Franz, Stockelsdorf (DE); Birger Landwehr, Lübeck (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 0 days.

(21) Appl. No.: 14/978,427

(22) Filed: Dec. 22, 2015

(65) Prior Publication Data
US 2016/0189518 A1    Jun. 30, 2016

(30) Foreign Application Priority Data
Dec. 24, 2014    (DE) .................. 10 2014 019 520

(51) Int. Cl.
*G08B 23/00*    (2006.01)
*A61B 5/00*    (2006.01)
*A61B 5/091*    (2006.01)

(52) U.S. Cl.
CPC .................. *A61B 5/00* (2013.01); *A61B 5/091* (2013.01); *A61B 5/746* (2013.01)

(58) Field of Classification Search
CPC combination set(s) only.
See application file for complete search history.

(56) References Cited

U.S. PATENT DOCUMENTS

| | | | |
|---|---|---|---|
| 3,559,638 A * | 2/1971 | Potter | A61B 5/097 600/540 |
| 4,413,632 A * | 11/1983 | Schlessinger | A61B 5/083 600/529 |
| 4,421,113 A | 12/1983 | Gedeon et al. | |
| 5,694,926 A * | 12/1997 | DeVries | A61M 16/125 128/204.21 |
| 5,865,736 A | 2/1999 | Baker, Jr. et al. | |
| 8,374,666 B2 | 2/2013 | Graboi et al. | |
| 8,430,817 B1 | 4/2013 | Al-Ali et al. | |
| 2002/0005197 A1 * | 1/2002 | DeVries | A61M 16/125 128/204.21 |
| 2009/0171167 A1 | 7/2009 | Baker, Jr. et al. | |

(Continued)

FOREIGN PATENT DOCUMENTS

DE    31 23 678 A1    4/1982

*Primary Examiner* — Travis Hunnings
(74) *Attorney, Agent, or Firm* — McGlew and Tuttle, P.C.

(57) ABSTRACT

A method for generating an alarm during the monitoring of a patient with the step of determining a minute volume (MVpat) of the patient, setting a minute volume lower limit (MVlow) and/or a minute volume upper limit (MVhigh), wherein the minute volume (MVpat) is cumulated by means of an increment function into a volume (Vdeficit_kum) when the measured value drops below the minute volume lower limit (MVlow) or exceeds the minute volume upper limit (MVhigh), and an alarm is triggered when the cumulated volume (Vdeficit_kum) exceeds a maximum allowable volume (Vdeficit_apn). Furthermore, the present invention pertains to a device for reducing clinically irrelevant alarms during the monitoring of a patient for carrying out the method according to the present invention.

11 Claims, 5 Drawing Sheets

(56) References Cited

U.S. PATENT DOCUMENTS

| | | |
|---|---|---|
| 2009/0209839 A1 | 8/2009 | Ochs et al. |
| 2009/0247851 A1 | 10/2009 | Batchelder et al. |
| 2011/0009710 A1 | 1/2011 | Kroeger et al. |
| 2011/0132368 A1 | 6/2011 | Sanchez et al. |
| 2013/0201020 A1* | 8/2013 | Mannheimer ...... A61B 5/02455 340/573.1 |

* cited by examiner

METHOD FOR GENERATING AN ALARM DURING THE MONITORING OF A PATIENT AND DEVICE THEREFOR

CROSS REFERENCE TO RELATED APPLICATIONS

This application claims the benefit of priority under 35 U.S.C. §119 of German Patent Application 10 2014 019520.1 filed Dec. 24, 2014, the entire contents of which are incorporated herein by reference.

FIELD OF THE INVENTION

The present invention pertains to a method for reducing clinically irrelevant alarms during the monitoring of a patient with the steps of: Determining a minute volume of the patient and setting a minute volume lower limit and/or a minute volume upper limit. The present invention pertains, furthermore, to a device for reducing clinically irrelevant alarms during the monitoring of a patient with a determination unit for determining a minute volume of the patient and with a setting unit for setting a minute volume lower limit and/or a minute volume upper limit.

BACKGROUND OF THE INVENTION

Current developments in medical engineering lead to an ever-increasing number of medical devices that are capable of generating alarm. As a result, the avoidance of clinically irrelevant alarms is also of ever-increasing significance. Clinically irrelevant alarms triggered too frequently are among the most dangerous technical risk factors in hospitals. The hazard potentials are numerous and varied. Alarm limits could be adjusted by the clinical staff to reduce the noise level outside their reasonable range and they may become ineffective as a result, or the acoustic volume of the alarm may be set at a barely perceptible minimum. The frequency of alarms could lead to an insidious desensitization of the clinical staff, so that there is a risk that the staff will not respond adequately to an actual hazard to the patient any more. Excessively frequent and medically irrelevant alarms may lead, furthermore, to annoyance, frustration and stress, which may in turn lead as a consequence to declining concentration as well as an impairment of the work performance and performance capacity. In addition, the work process of the clinical staff could be disturbed or interrupted, so that important activities, e.g., the medication of a patient, may be temporarily forgotten, or errors may be creep up on resumption.

On the other hand, a smaller number of alarms increases at the same time the attentiveness to the now prominently relevant alarms and markedly increases the patient's safety at the same time. Furthermore, the care becomes more efficient, because it can be carried out trouble-free and, in addition, more time is available at bedside. Fewer alarms also mean a reduction of the stress level, more restful sleep and faster recovery for the patient, which results in a shorter hospital stay.

As long as there is no contraindication and additional clinical parameters that are taken into consideration, for example, the oxygen saturation or the $CO_2$ partial pressure, are within an acceptable range during the monitoring of the respiratory activity, immediate alarming is dispensable, at least if the limit values are transgressed only briefly and/or slightly.

Methods and devices for avoiding clinically irrelevant alarms, in which the distinction between clinically relevant and clinically irrelevant alarms is performed on the basis of the minute volume, are known for this from the state of the art. The minute volume is used as a standard in medicine. In mandatory ventilation, the minute volume corresponds to the product of the tidal volume applied by the respiration rate with the unit liters per minute. Thus, a minute volume of 9 L/minute is obtained, for example, from a set tidal volume of 600 mL and a respiration rate of 15 per minute. An (expiratory) time volume corresponds in this case to the quantity of the (exhaled) air flow over a defined time period.

Since the minute volume is an important indicator for the ventilation of the patient, monitoring of the value by ventilators used in intensive care is obligatory. If the resulting minute volume is constant and hence available at any time during mandatory ventilation, an exact result can be calculated in case of spontaneous breathing, purely theoretically, only by integrating the last flow value at the end of the time interval of one minute. However, this may also take place over shorter time intervals and extrapolated to one minute. Since the result reflects both breathing efforts made by the patient immediately before and those that had occurred already a minute ago, the current respiratory activity and possible hazards, e.g., hypopnea, can be inferred from a minute volume calculated in this way only conditionally.

Consequently, the calculated minute volume should generally be, on the one hand, an indicator of the current respiratory activity and thus fast enough for changes to be reflected in the value within a short time. On the other hand, the minute volume should be slow enough for individual breaths to affect the value only slightly and consequently for the time course of the minute volume to have only a slight "waviness." Based on the different lung constants of adults, children and new and premature babies, the concrete design of the filter used for the calculation is adapted, as a rule, to the particular patient categories. Prior-art filters generate as a signal a step response. The time characteristics of the output signal of a transmission member, for example, of the filter, in case of a change in the signal at the input is described as a step response, so that the filter characteristic can be unambiguously characterized on the basis of this step response. A time value T90, which is linked with this, indicates the time after which 90% of the maximum of the output value was reached. The T90 value is correspondingly an indicator of the delay with which the input signal affects the output signal. A shortening of the T90 time is associated, in general, with increased oscillations on the output signal.

The signals generated by are usually processed in conventional medical devices in a monitoring device. Such monitoring devices have, in turn, a monitoring range, which can be divided, in principle, into at least two ranges: An alarm-free range (desired range) and into one or more ranges in which an alarm is mandatory. Both arise directly from explicitly settable or derived alarm limits. The monitoring of a measured value, for example, a minute volume, leads, as a rule, directly to an alarm as soon as a measured value exceeds or drops below a limit value, i.e., the measured value moves from the alarm-free range into the alarm-requiring range (cf. FIG. 1).

In conventional alarm methods and devices, the minute volume is monitored on the basis of exactly such a lower limit and upper limit, which can be set and adjusted by the user at any time. The alarm limits are set individually for each patient and depend especially on his physical constitution and medical condition. A corresponding alarm is triggered and produced by the device acoustically as well as optically exactly as soon as the current value of the minute volume is below the set lower alarm limit (MV-low) or above the set upper alarm limit (MV-high). In clinical practice, an alarm limit is occasionally transgressed only briefly and/or only very slightly. This is due, for example, to the deterioration of the physiological regulation of respiration or to movement of the patient. The latter may occasionally lead to a short-term slippage of the breathing mask, so that the exhaled lung volume is not detected by the ventilator and the determined minute volume is thus smaller than it actually is.

By setting an alarm delay (MVdelay), it is possible in such case that the alarm will not be triggered immediately after the measured value drops below MVlow. Alarms based on brief transgressions of the limits can thus be effectively suppressed. With the aim of avoiding false alarms occurring during the monitoring and of reducing the number of alarms hereby, delay times (MVdelay) set as fixed values or delay times that can be set by the user can already be set on some ventilators to briefly suppress alarms. However, it is problematic in connection with the setting of such delay times that the particular course of the values of the minute volume cannot be accessed. Depending on the patient's condition, clinical picture, individual constitution, etc., and on the extent by which the measured value exceeds or drops below the limit value, delay times of different duration are needed in order to effectively rule out a risk, on the one hand, but not to generate a needlessly early alarm, on the other hand.

SUMMARY OF THE INVENTION

An object of the present invention is therefore to take the above-described problem at least partially into account with a method as well as with a device therefor. An object of the present invention is, in particular, to provide a method for reducing clinically irrelevant alarms during the monitoring of a patient as well as a device therefor. In addition, an object of the present invention is to continue to attain a high sensitivity in monitoring the expiratory minute volume, for which already existing, patient-specific settings of a ventilation can preferably be used to adapt the alarm characteristic to the particular situation of the patient as optimally as possible without additional inputs performed by a user.

It is essential in this connection that a reduction of clinically irrelevant alarms is achieved compared to prior-art technical solutions. Features and details that are described in connection with the method also apply, of course, in connection with the device used therefor according to the present invention and vice versa, so that reference is and can always mutually be made concerning the disclosure regarding the individual aspects of the present invention.

According to a first aspect according to the present invention, a method for reducing clinically irrelevant alarms during the monitoring of a patient has the following steps: Determination of a minute volume of the patient and setting of a minute volume lower limit and/or of a minute volume upper limit, wherein the minute volume is cumulated to a volume by means of an increment function when the measured value drops below the minute volume lower limit or exceeds the minute volume upper limit, and an alarm is triggered when the cumulated volume exceeds a maximum allowable volume.

When monitoring the minute volume, the cumulated volume is a good criterion for distinguishing between clinically relevant and irrelevant alarms. The cumulated volume describes the volume deficiency or the volume excess that builds up due to an insufficient or excessive ventilation compared to normal breathing. The volume depends in this context on both the duration and the severity of hypoventilation or hyperventilation. The volume corresponds to a volume deficiency in case of hypoventilation and to volume excess in case of hyperventilation.

The minute volume can be determined by detecting a patient flow and patient characteristics and by integrating the patient flow and the patient characteristics over a defined time interval. More precisely, for example, a tidal volume and a respiration rate of the patient are detected. The minute volume can then be calculated from a product of the tidal volume and the respiration rate.

The maximum allowable volume is set according to the present invention as a product of a defined time and the set minute volume lower limit or the set minute volume upper limit. A maximum allowable volume deficiency corresponds, for example, to apnea over a defined time period, without a health risk having to be expected. The defined time can be derived from already defined settings, such as a time for an apnea alarm or a set backup frequency, which can be derived, for example, from the set respiration rate for mandatory ventilation breaths.

In case of hypoventilation, during which a defined but nevertheless insufficient air exchange is still present compared to apnea, the time needed for building up the same volume or, in this case, the same volume deficiency increases. If the volume deficiency is assumed to be tolerable, an alarm should only be triggered if this volume deficiency is exceeded. Since the volume deficiency builds up more slowly in case of reduced lung function than in case of apnea, this also causes a corresponding alarm to be activated only later. Thus, the suppression of the alarm is not fixed, but depends on both the minute volume lower limit and upper limit and the defined time. Compared to an alarm suppression on the basis of a settable alarm delay, which does, however, depend on the respiratory activity and is consequently a fixed alarm delay, this leads to a higher specificity of the generated alarms. According to the present invention, the duration of the alarm suppression consequently depends on the individual respiratory activity, during which a defined volume, for example, a volume deficiency, is built up. An alarm can then be suppressed over precisely this duration. An alarm is generated and outputted acoustically and/or optically only at the time at which the maximum allowable volume is exceeded. However, the present invention is not limited to this. It is also conceivable, for example, that an alarm is triggered already when the maximum allowable volume is reached.

The product concerning the maximum allowable volume may be multiplied according to the present invention by an adjusting factor. As a result, it is possible in an especially simple way to flexibly adapt the maximum allowable volume to the particular patient or defined measuring conditions.

According to another aspect of the present invention, the value of the cumulated volume can be stored and held and reduced by a defined value step by step by means of a decrement function before the maximum allowable volume is reached and after the minute volume lower limit is again exceeded or the measured value drops again below the minute volume upper limit. Due to the fact that the cumulated volume is not reset immediately to 0 in case the minute volume values return again into the alarm-free desired range, it is possible, for example, even in case of minute volume values alternating around the lower limit or upper limit to generate an alarm in time and rapidly. The reduction may occur, for example, continuously corresponding to the cumulated difference from any set value limit. If, for example, the cumulated volume deficiency drops again below the preset limit, i.e., a maximum allowable volume and thus leaves the alarm-free range, the volume deficiency is again built up from its last existing value. This means that the volume deficiency increases again in this case by the difference from the corresponding set value limit. It is preferable in this context that the stepwise reduction of the cumulated volume be performed more rapidly or more slowly than the buildup of the cumulated volume. This means that the step size for the decrementing may differ from that for the incrementing. A possible "oscillation" of the alarm system can be prevented hereby. It is preferable in this connection that the value of the volume deficiency not become negative, i.e., the decrement function is ended as soon as the cumulated volume equals 0.

Independently of the cause of triggering of the alarm, it may be advantageous that the cumulated volume will not be cumulated any longer when the maximum allowable volume and the alarm generation associated therewith are reached. The current value is stored, instead, and is reduced again step by step by means of the decrement function according to the selected instruction only with the return into the alarm-free range. This ensures that if the measured value returns into the alarm-free range only briefly and then leaves the desired range again, an alarm is triggered more rapidly, but not immediately, and this happens depending on the patient's volume deficiency, which was already reduced before. The alarm suppression can be shortened hereby when the patient's respiratory activity is normalized only briefly.

As an alternative, the cumulated volume can be further cumulated when the maximum allowable volume is exceeded. This can additionally increase the patient's safety in the respect that the volume deficiency, which continues to be present in the patient, is used even clearly after the limit is exceeded. This means that when the patient's respiratory activity becomes normalized only briefly, an alarm is triggered immediately in case the limit value is violated, because the currently cumulated volume still markedly exceeds the maximum allowable volume.

According to another aspect of the present invention, a lower minute volume alarm limit and/or an upper minute volume alarm limit can be set, which are above the minute volume upper limit and below the minute volume lower limit, which are set, for example, by a user, and an alarm can be triggered when the measured value drops below the lower minute volume alarm limit or exceeds the upper minute volume alarm limit, independently of the exceeding of the maximum allowable volume. The minute volume alarm limits are selected in this case to be such that when the measured value exceeds or drops below them, the maximum allowable volume is exceeded independently of the further course of the minute volume. Such an additional mandatory alarm limit can be determined automatically. It is used to guarantee that alarming will take place in time in case of a greatly decreasing minute volume due, for example, to apnea. The lower minute volume alarm limit is directly correlated here with the minute volume lower limit and the defined time for the apnea alarm limit (or other derived times). The upper minute volume alarm limit is directly correlated with the minute volume upper limit and the defined time that correspondingly belongs to it. For example, the longer the duration of the apnea that is tolerated by the patient and is permissible and is set on the device, the lower will be the value of the lower minute volume alarm limit. This value may form, for example, the lower saddle point of the minute volume values. Since the minute volume alarm limits depend clearly on the set values of the minute volume limits and the defined time as well as the filter being used, the values can be determined efficiently, for example, on the basis of a suitable hash table.

Furthermore, it is possible that the currently cumulated volume is represented in relation to the maximum allowable volume by means of a user interface. Irritations, which could arise from the circumstance that the user expects an alarm in case an alarm limit is violated, can be avoided by such a representation, which is, for example, a graphic representation. Elements, which show this relationship to the user, for example, by means of a bar graph or a pie chart, can be displayed for this by the user interface.

Furthermore, a visual and/or acoustic alarm can be triggered by the user interface when the measured value drops below the minute volume lower limit or exceeds the minute volume upper limit and/or when the measured value exceeds the maximum allowable volume difference. Approaching the limits may also be visualized, for example, by a conspicuous blinking and/or a change in the color of a bar. This means that a color marking may illustrate, for example, the degree of severity of the existing volume deficiency. The display elements may preferably be displayed together with the measured values for the minute volumes in the same parameter field. It is likewise possible that the fact that a measured value drops below the minute volume lower limit or exceeds the minute volume upper limit leads at first only to a visual indication on the device and it generates a visual and/or acoustic alarm only when the maximum allowable volume is exceeded.

According to another aspect of the present invention, a device for reducing clinically irrelevant alarms during the monitoring of a patient has a determination unit for determining a minute volume of the patient and a setting unit for setting a minute volume lower limit and/or a minute volume upper limit. The device according to the present invention has, furthermore, a comparison unit, by which the minute volume can be cumulated to a volume by means of an increment function when the measured value drops below the minute volume lower limit or exceeds the minute volume upper limit, and an alarm unit, by which an alarm can be triggered when the cumulated volume exceeds a maximum allowable volume.

It is possible due to the device according to the present invention to provide a monitoring and alarm device, in which an alarm signal is generated both depending on a duration and a severity of hypoventilation or hyperventilation. The suppression of an alarm is not fixed, but depends on the minute volume lower limit and upper limit. Compared to an alarm suppression on the basis of a settable alarm delay, which is, however, independent of the respiratory activity and is consequently a fixed alarm delay, this leads to a higher specificity of the alarms generated by the device. All the advantages that were described in connection with the method according to the present invention correspondingly also apply to the device according to the present invention.

To determine the minute volume, the device according to the present invention may have a detection unit for detecting a patient flow and patient characteristics and a computer for calculating the minute volume by integrating the patient flow and the patient characteristics over a defined time interval. The device according to the present invention may have for this, for example, a detection device for detecting a tidal volume and a respiration rate of the patient. Further, the device may have a computer for calculating the minute volume from the product of the tidal volume and the respiration rate.

In a variant, the device according to the present invention may have a user interface, by which the currently cumulated volume can be represented in relation to the maximum allowable volume. Irritations, which arise from the circumstance that a user expects an alarm in case of a violation of an alarm limit, can be avoided hereby. The user interface may have for this display elements, which display this relationship to the user graphically, for example, by means of a bar graph or a pie chart.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
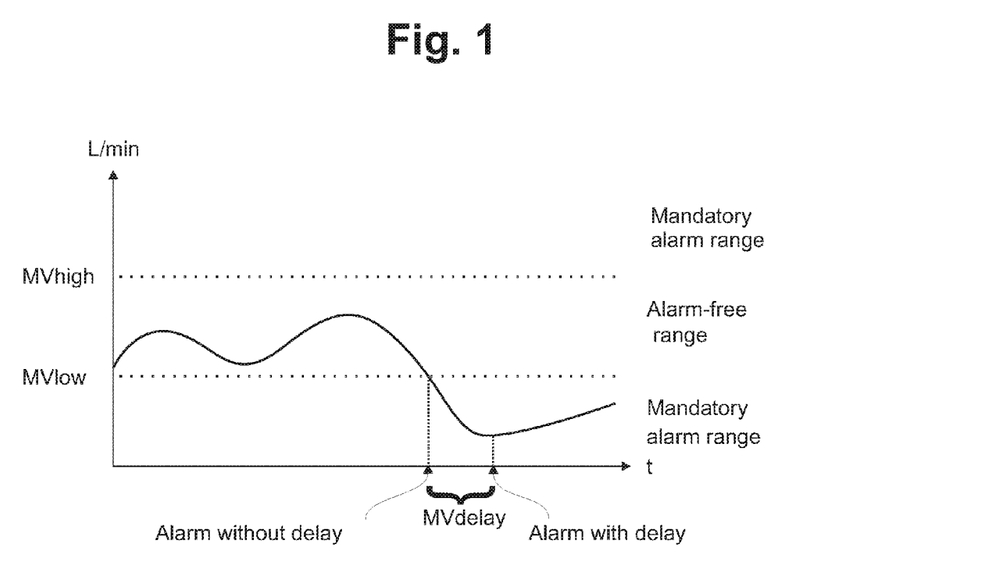
FIG. 1 is a graphic representation of a signal characteristic of a measured minute volume between ranges in which alarm is mandatory and an alarm-free range.

Referring to the drawings, FIG. 1 shows a graphic representation of a signal characteristic of a measured minute volume MVpat between ranges in which an alarm is mandatory and an alarm-free range according to a diagram known in the state of the art. The abscissa shows the time and the ordinate shows a minute volume in L per minute (L/min). The monitoring range of the diagram shown in FIG. 1 can be divided, in principle, into two ranges: A range in which an alarm is mandatory (desired range) and an alarm-free range. Both ranges are defined directly by the explicitly settable or derived alarm limits MVlow, MVhigh. The monitoring of the measured values usually leads directly to an alarm in the systems known from the state of the art as soon as a measured value exceeds or drops below a limit value, i.e., when the measured value moves from the alarm-free range into the range in which an alarm is mandatory.

In conventional systems, the minute volume MVpat is monitored precisely on the basis of such a lower and/or upper alarm limit MVlow, MVhigh, which can usually be set and adjusted by the user at any time. The alarm limits MVlow, MVhigh are set individually for each patient and depend especially on the patient's physical constitution and medical condition. A corresponding alarm is triggered and outputted acoustically as well s optically exactly as soon as the current value of the minute volume MVpat is below the lower set limit MVlow or above the upper set limit Mvhigh.

Further, it is known in the state of the art that by setting an alarm delay MVdelay, the alarm is not triggered immediately after the measured value drops below or exceeds the alarm limits. Especially brief transgressions of the limits can be suppressed hereby. However, it was found that such a delay set in a fixed manner lacks sufficient specificity regarding different alarm patterns of different patients.

An improved method is therefore proposed according to the present invention for reducing clinically irrelevant alarms during the monitoring of a patient. A triggered alarm can be considered to be clinically irrelevant if and only if the patient's condition is known and no change (exacerbation) of this condition has since been detected, or when the alarm failed to lead to any clinical action. For example, the minute volume being monitored, MVpat, could briefly exceed or drop below a limit value set in the device during irregular breathing without the patient being actually at risk thereby. Alarm generation would be undesired in such a case and in case of transient artifacts.

Experiments carried out in connection with the present invention show that a cumulated volume, for example, the so-called cumulated volume deficiency Vdeficit_kum, represents a good criterion for distinguishing between clinically relevant and irrelevant alarms during the monitoring of the minute volume Mvpat.

It should be noted in this context that the present invention pertains to both a cumulated volume deficiency and a cumulated volume excess. To simplify the detailed description that follows, reference will, however, be made especially to the cumulated volume deficiency in reference to FIGS. 2 through 7.

Figure 2:
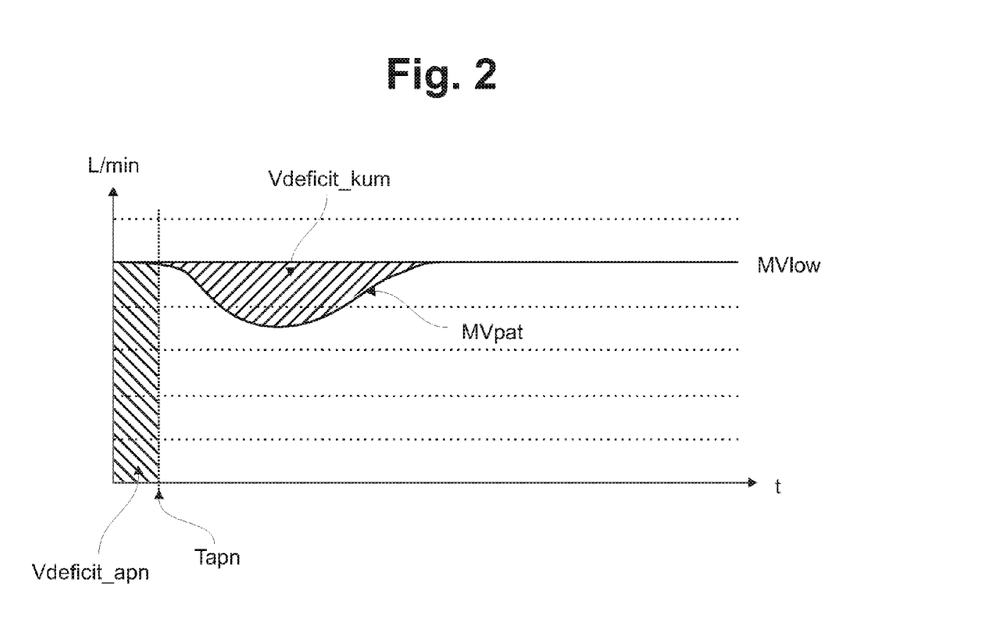
FIG. 2 is a graphic representation of a signal characteristic of a measured minute volume in the presence of apnea.

The cumulated volume deficiency Vdeficit_kum shown in FIG. 2 describes the volume deficiency that builds up due to an insufficient ventilation compared to normal breathing. The volume deficiency depends on both the duration and the severity of the hypoventilation. The value of a maximum allowable volume, called maximum allowable volume deficiency Vdeficit_apn in FIG. 2, corresponds to apnea over a defined time, even though no health risk can be expected.

The area of the cumulated volume deficiency Vdeficit_kum corresponds in FIG. 2 to the area of the maximum allowable volume deficiency Vdeficit_apn. Monitoring with respect to this special case can be embodied on conventional ventilators by means of an apnea monitoring, in which case an alarm limit can be set as a defined time Tapn. The time needed to build up the same volume deficiency is prolonged in case of hypoventilation, during which a defined, albeit insufficient exchange of air does nevertheless take place compared to apnea.

The maximum allowable volume deficiency Vdeficit_apn can be determined as follows:

$$Vdeficit\_apn = MVlow * Tapn * Fapn,$$

in which MVlow is a minute volume lower limit, Tapn is a maximum apnea time, and Fapn is a factor for adjusting the maximum allowable volume deficiency Vdeficit_apn. The defined time Tapn can also be derived here from other settable time criteria, e.g., a backup frequency, for example, Tapn=1/backup frequency.

In case of a minute volume of 10 L/min and 167 mL/sec taken as an example and a breathing interruption or a defined apnea time of 8 sec, a volume deficiency of 1,333 mL will build up based on $$V\text{deficit\_apn}=MV\text{low}*T\text{apn}=167 \text{ mL/sec}*8 \text{ sec.}$$

The adjustment factor shall be Fapn=1 here for simplification.

If the cumulated volume deficiency Vdeficit_kum is considered to be allowable, an alarm should only be triggered when this is exceeded. Since the volume deficiency is building up more slowly in case of reduced lung function, this causes a corresponding alarm to be activated only later. The suppression of the alarm is not consequently fixed, but it depends on the selected minute volume lower limit MVlow as well as the defined time, e.g., Tapn. This leads to a higher specificity of the generated alarms compared to alarm suppressions on the basis of an alarm delay MVdelay that can be set but is independent of the respiratory activity and is consequently fixed.

Based on the filtering of the measured flow values, which is described in the introduction to the description, changes in the patient's breathing are reflected by the calculated minute volume MVpat after some time only; the value consequently drops only with a delay after the beginning of the apnea. Yet, the volume deficiency arising herefrom is independent of the time course, which is preset by the filter constants. The volume deficiency Vdeficit_kum, which can be calculated from the cumulated difference of MVlow and MVpat, corresponds exactly to the apnea volume deficiency.

Figure 3:
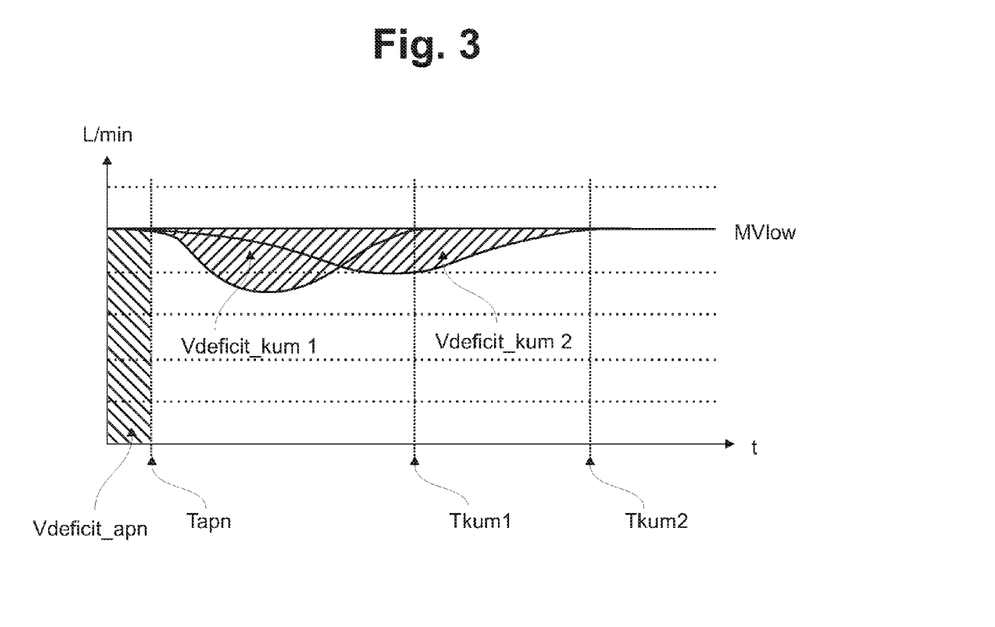
FIG. 3 is a graphic representation of a different buildup of a volume deficiency and of an alarm suppression in case of a deviating respiratory activity of a patient.

FIG. 3 shows the method according to the present invention for the case of hypopnea. In this case, in which the patient's breathing does not come completely to a standstill, the cumulating volume deficiency Vdeficit_kum 2 is distributed over a longer period of time than in case of an at least imminent apnea, during which the cumulating volume deficiency Vdeficit_kum 1 is distributed over a shorter period of time. The alarm Tkum 1 is correspondingly delayed over a shorter time in case of the at least imminent apnea than is the alarm Tkum 2 in case of hypopnea. The duration of the alarm suppression consequently depends especially on the individual respiratory activity, during which a defined volume deficiency, in this case the maximum allowable volume deficiency Vdeficit_apn, is built up. An alarm would in this case be suppressed over precisely this duration.

Figure 4:
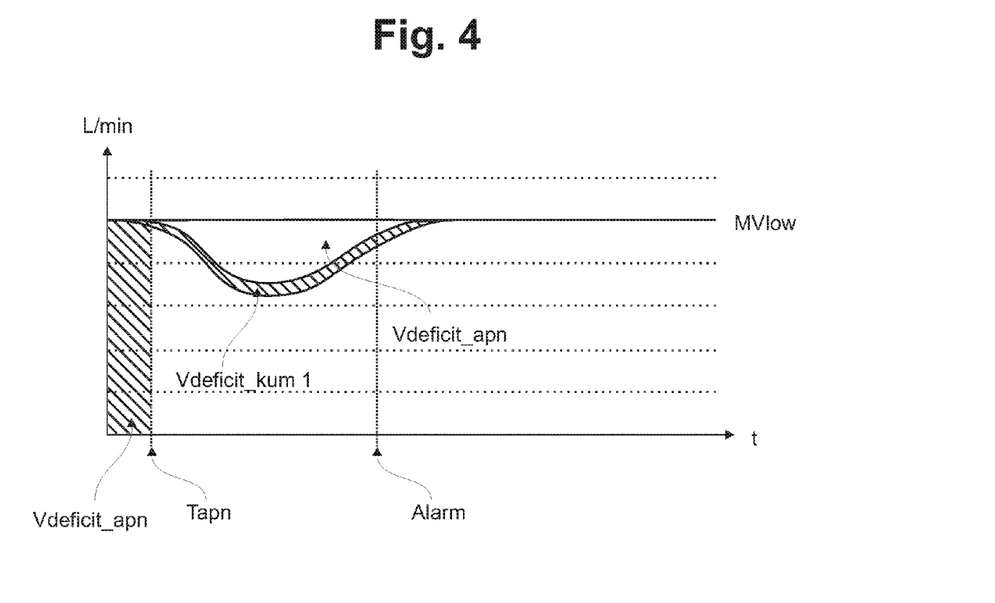
FIG. 4 is a graphic representation of an alarm generation according to one embodiment of the present invention.

An alarm generation according to an embodiment of the present invention will now be described with reference to FIG. 4. If the cumulating volume deficiency Vdeficit_kum increases independently of the particular case and its value becomes higher than the maximum allowable volume deficiency Vdeficit_apn, an alarm is generated immediately and outputted, for example, acoustically and/or optically if it exceeds the maximum allowable value. The alarm time shown in FIG. 4 does not mean in this context that an alarm is triggered at this time only, but rather that an alarm will be triggered beginning from this time, at least as long as the minute volume MVpat is below the minute volume lower limit MVlow and the cumulated volume deficiency Vdeficit_kum is greater than the maximum allowable volume deficiency Vdeficit_apn. This means that an alarm is triggered when the patient is breathing very weakly over a rather long period of time, but no apnea situation was detected.

The above-described method according to the present invention can be complemented by further functions to optimize the time course and to increase the patient's safety as a result.

Figure 5:
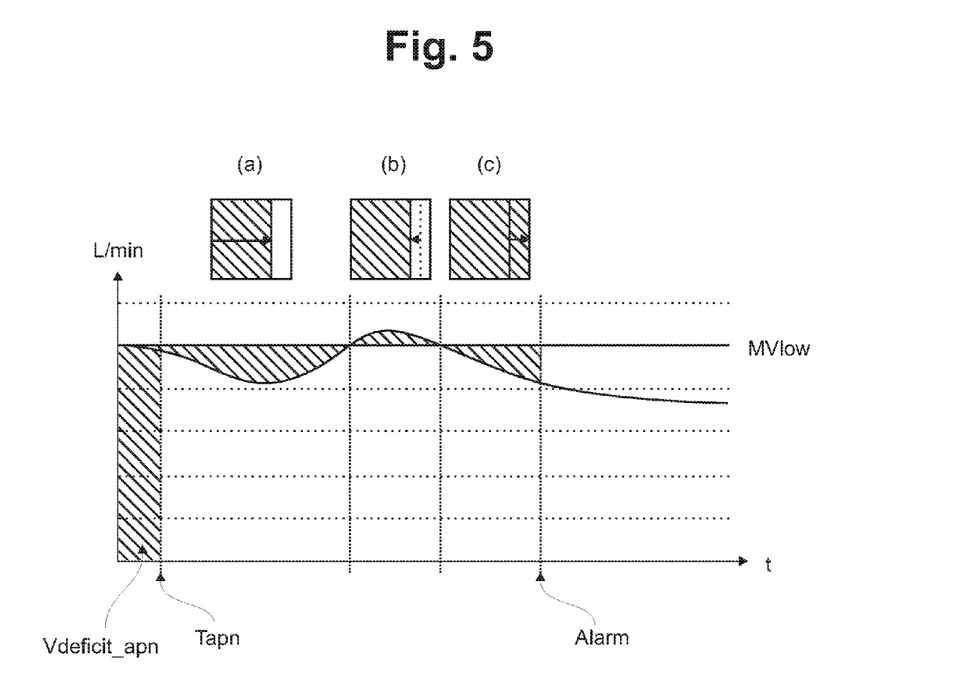
FIG. 5 is a graphic representation of an alarm generation by means of a decrement function in case of alternating minute volume measured values according to another embodiment of the present invention.

FIG. 5 shows, for example, an alarm generation by means of a decrement function in case of alternating minute volume measured values according to another embodiment of the present invention.

In order to make it nevertheless possible to generate an alarm in time and rapidly in case of alternating minute volume values MVpat around a limit value MVlow, the cumulated volume deficiency Vdeficit_kum is not set back to 0 immediately when the minute volume value MVpat returns into the (alarm-free) desired range. The cumulated volume deficiency Vdeficit_kum is reduced, instead, in general, continuously by a defined value. This reduction may take place, for example, continuously, corresponding to the cumulated difference from any desired set value limit. If the cumulated volume deficiency Vdeficit_kum drops again below the preset limit and thus leaves the alarm-free range, the volume deficiency Vdeficit_kum is built up again from its last existing value, i.e., the volume deficiency Vdeficit_kum rises again in this case by the difference from the corresponding set value limit.

As is shown in FIG. 5 under (a), the volume deficiency Vdeficit_kum builds up from MVlow while the minute volume MVpat is below MVlow. As is shown under (b), the volume deficiency Vdeficit_kum is not abolished completely when the measured value exceeds MVlow and the minute volume MVpat consequently returns into the desired range, but is reduced step by step corresponding to the respiratory activity, which is above the limit. The stepwise reduction does not, in this context, have to be the same as for the incrementing. When the measured value drops again below MVlow, the volume deficiency Vdeficit_kum is built up again, as shown under (c), and an alarm is triggered when the maximum allowable volume deficiency Vdeficit_apn is reached or exceeded. The value of the volume deficiency cannot according to this embodiment, in general, become negative, i.e., the decrement function is ended as soon as the volume deficiency equals 0. However, other embodiments may be provided and the present invention is not limited to the particular embodiment.

It is possible in this connection that the cumulating volume deficiency Vdeficit_kum will not be cumulated further when the maximum allowable volume deficiency Vdeficit_apn is exceeded and an alarm is consequently generated, independently of the cause by which the alarm is triggered. The current value can be maintained, instead, and can be reduced again according to a selected instruction or stepwise by means of a decrement function only when it returns into the alarm-free range. This ensures that, independently of the patient's volume deficiency, which was already reduced before, an alarm is generated more rapidly, but not immediately in case of an only brief return into the alarm-free range, after which the measured (value) will again leave the desired range. This means that the duration of the alarm suppression becomes shorter when the respiratory activity of the patient becomes normal only briefly.

As an alternative, the cumulating volume deficiency Vdeficit_kum can also be cumulated continuously further when the maximum allowable volume deficiency Vdeficit_apn is exceeded. This additionally increases the patient's safety in the respect that the volume deficiency, which continues to be present in the patient. is used even clearly after the limit has been exceeded. This means that when the patient's respiratory activity becomes normal only briefly, an alarm is generated immediately if the limit value is transgressed, because the currently cumulated volume deficiency Vdeficit_kum still clearly exceeds the maximum allowable volume deficiency Vdeficit_apn.

Figure 6:
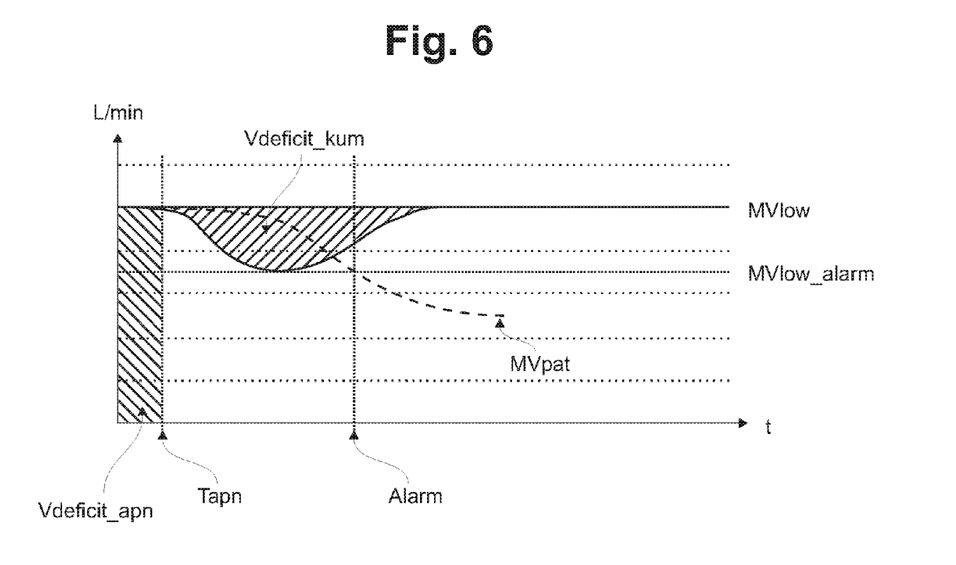
FIG. 6 is a graphic representation of an alarm generation in case a measured value drops below a lower minute volume alarm limit according to another embodiment of the present invention.

FIG. 6 shows a graphic representation of an alarm generation in case the measured value drops below a lower minute volume alarm limit MVlow according to another embodiment of the present invention. The mandatory minute volume alarm limit, for example, the lower minute volume alarm limit MVlow_alarm in FIG. 6, which can be automatically determined, is used to guarantee early alarm generation in case of very weak breathing without apnea. An alarm is triggered in this case in an anticipatory manner already when the volume deficiency Vdeficit_apn is exceeded. As can be seen in FIG. 6, the lower minute volume alarm limit MVlow_alarm is below the minute volume lower limit MVlow and is directly correlated with the minute volume lower limit MVlow and the defined time Tapn (or with the value derived from the backup frequency). The longer, for example, the allowable duration of apnea defined for the patient, the lower becomes the value of the lower minute volume alarm limit MVlow_alarm. The value of the lower minute volume alarm limit MVlow_alarm forms in this case at the same time the lower saddle point of the values of the minute volume Mvpat.

When the initially measured minute volume value MVpat drops below the lower minute volume alarm limit MVlow_alarm, an alarm is triggered immediately. This happens even in the case in which the maximum allowable volume deficiency Vdeficit_apn was not yet reached at this point in time, but it can already be assumed based on the filter characteristic that the cumulating volume deficiency Vdeficit_kum will exceed the maximum allowable volume deficiency Vdeficit_apn independently of the further course of the minute volume MVpat. Since the lower minute volume alarm limit MVlow_alarm depends on the set values of the minute volume lower limit MVlow, the defined time Tapn and the filter being used, it is also possible according to the present invention that the values can be efficiently determined on the basis of a suitable hash table.

Figure 7:
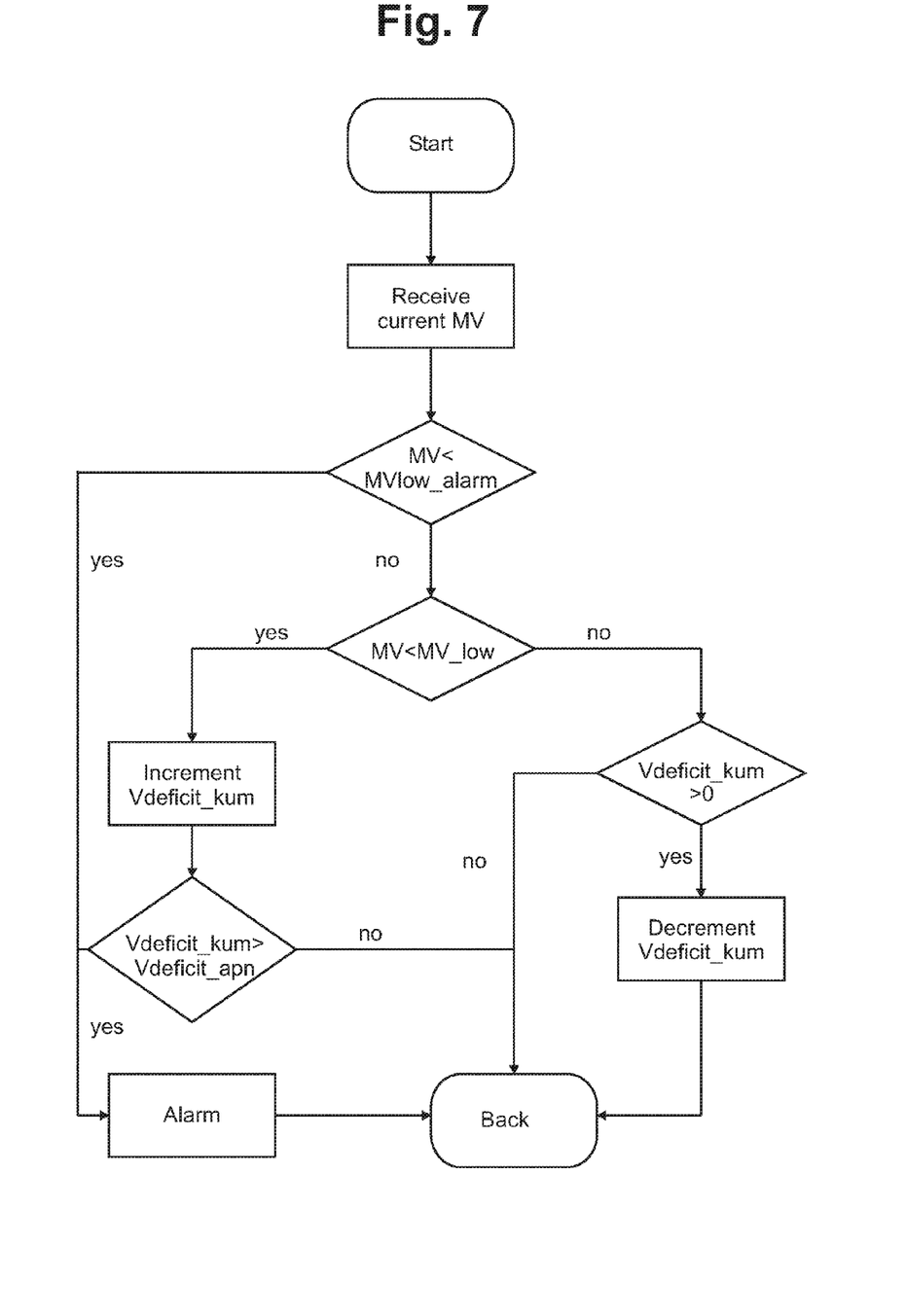
FIG. 7 is a flow chart representing a method according to the present invention.

FIG. 7 shows a flow chart for carrying out the method according to the present invention in case of apnea or hypopnea. As was described above in detail, values of the minute volume MVpat are first obtained. It is then decided whether the minute volume MVpat is higher or lower than the lower minute volume alarm limit MVlow_alarm or not. If the minute volume MVpat is lower than the lower minute volume alarm limit MVlow_alarm, an alarm is immediately triggered. If the minute volume MVpat is higher than or equal to the lower minute volume alarm limit MVlow_alarm, a check is performed to determine whether the minute volume MVpat is lower than the minute volume lower limit MV_low. If yes, the cumulated volume deficiency Vdeficit_kum is formed on the basis of an increment function. A check is subsequently performed in this case to determine whether the cumulated volume deficiency Vdeficit_kum is greater than the maximum allowable volume deficiency Vdeficit_apn. If yes, an alarm is triggered without delay. If not, the routine is ended or started anew. If it is determined concerning the check of whether the minute volume MVpat is lower than the minute volume lower limit MV_low that it is not so, a further check is performed to determine whether a cumulated volume deficiency Vdeficit_kum is already available. If not, the routine is ended or started anew. However, if this is so, the present cumulated volume deficiency Vdeficit_kum is reduced step by step by means of a decrement function, optionally until no volume deficiency is present any more. The routine is subsequently ended or started anew.

Even though especially a lower limit value transgression is shown in FIGS. 2 through 7, the present invention is not limited to this. The present invention may rather be used analogously in case of a hyperventilation of the patient and hence in case of an upper limit value transgression. This means that a minute volume upper limit MVhigh is applicable instead of the minute volume lower limit MVlow, and an upper minute volume alarm limit MVhigh_alarm is to be taken into consideration instead of the lower minute volume alarm limit MVlow_alarm. Instead of a volume deficiency, one correspondingly speaks in this case of a volume excess, i.e., a respiratory activity of the patient that is above the permissible limit. The risk for the patient is not so great in case of hyperventilation as in case of a volume deficiency occurring to the same extent due to apnea or hypopnea. Therefore, reliable alarm generation can be assumed if the model of the volume deficiency is likewise used for the value of the maximum allowable volume excess. The risks of volutrauma or barotrauma during a short-term hyperventilation can be further minimized in this case by the standard monitoring of the tidal volume and of the ventilation pressure. However, the value of the maximum allowable volume excess can also be set to any other desired value.

Figure 8:
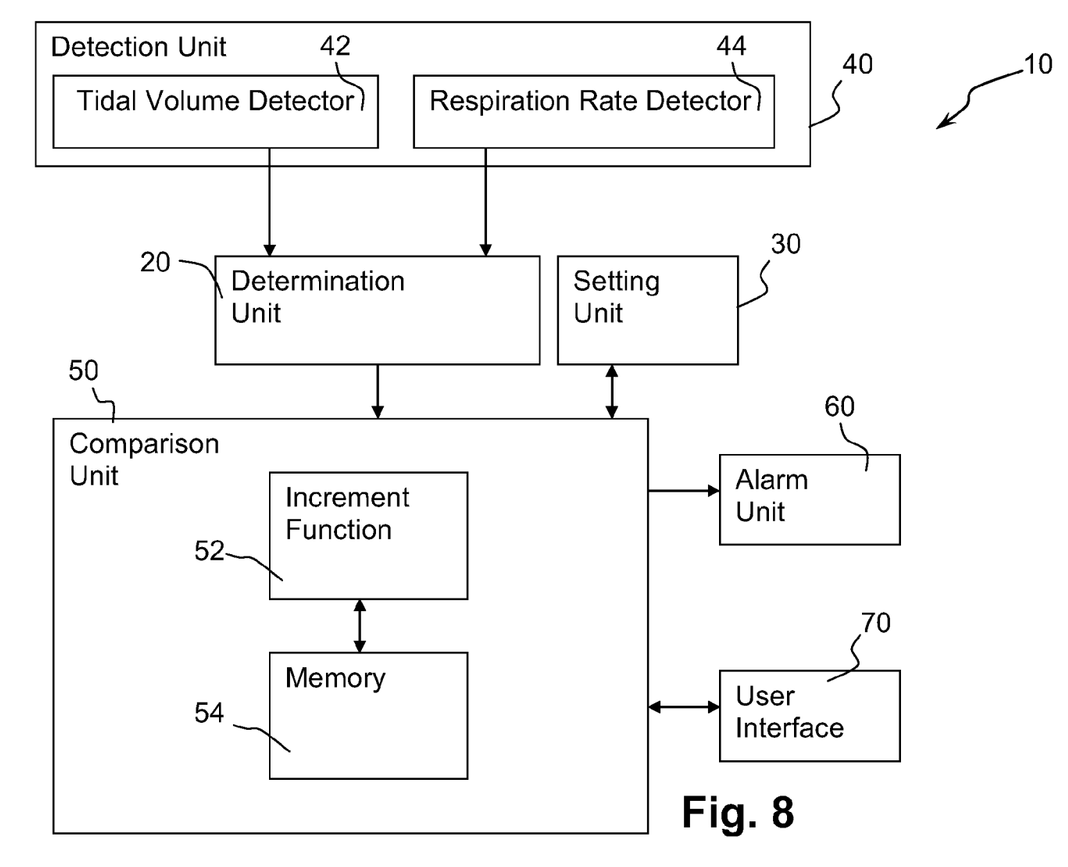
FIG. 8 is a schematic view of a device for reducing clinically irrelevant alarms during the monitoring of a patient according to the present invention.

Furthermore, a device 10 for reducing clinically irrelevant alarms during the monitoring of a patient is provided according to the present invention (FIG. 8). The device 10 comprises a determination unit 20 for determining a minute volume of the patient as well as a setting unit 30 for setting a minute volume lower limit MVlow and/or a minute volume upper limit MVhigh. In addition, the device contains a comparison unit 50, by which the minute volume MVpat can be cumulated by means of an increment function 52 when the measured value drops below the minute volume lower limit MVlow or the minute volume upper limit MVhigh is exceeded. The increment function 52 may also provide a decrement function by which the value of the cumulated volume may be stored in a memory 54 and reduced step by step by a defined value by means of the decrement function before the maximum allowable volume is reached and after the minute volume lower limit is exceeded or after the measured value drops again below the minute volume upper limit. The device 10 further includes an alarm unit 60, by which an alarm can be triggered when the cumulated volume Vdeficit_kum exceeds a maximum allowable volume Vdeficit_apn.

To determine the minute volume, the device according to the present invention may have a detection unit 40 for detecting a patient flow or patient values and a computer for calculating the minute volume by integrating the patient flow and the patient characteristics over a defined time interval. The device according to the present invention may have for this, for example, a tidal volume detection device 42 for detecting a tidal volume and a respiration rate detection device 44 for detecting a respiration rate of the patient. Furthermore, the device 10 may have a computer as the detection unit 40 for calculating the minute volume from the product of the tidal volume and the respiration rate. Individual computers or processors may be provided for the various functional units or a single computer or processor may provide the functional units.

In a preferred embodiment, the device according to the present invention is equipped with a user interface 70, by which the currently cumulated volume Vdeficit_kum can be represented in relation to the maximum allowable volume Vdeficit_apn. The user interface 70 may have for this display elements, which show this relationship to the user by means of a bar graph, as it is shown in FIG. 5 under (a) through (c), or a pie chart. The approach of defined limits can be reflected, for example, by a conspicuous blinking and/or a change in the color of a bar, i.e., a color marking illustrates the degree of severity of the existing volume deficiency. In a preferred embodiment of the present invention, the display elements may be represented together with the measured values for the minute volumes in the same parameter field.

While specific embodiments of the invention have been shown and described in detail to illustrate the application of the principles of the invention, it will be understood that the invention may be embodied otherwise without departing from such principles.

APPENDIX

List of Reference Symbols

MVlow Minute volume lower limit
MVhigh Minute volume upper limit
Mvlow_alarm Lower minute volume alarm limit. Alarm is triggered without time criterion when the measured value drops below the limit.
Mvhigh_alarm Upper minute volume alarm limit. Alarm is triggered without time criterion when the measured value exceeds the limit.
Mvpat Mean value of the minute volume determined at the patient by means of filter.
Mvdelay The delay time that can be set on the device regarding an alarm generation.
Vdeficit_apn The maximum allowable value for the patient (maximum allowable volume deficiency or maximum allowable volume excess). Vdeficit_kum Cumulated volume deficiency. Volume missing for sufficient ventilation, which increases while the measured value is below the MVlow alarm limit.
Tapn Defined time for apnea alarm limit.
Tkum1, Tkum2 Time during which a maximum allowable volume deficiency is reached.
Fapn Factor for adjusting Vdeficit_apn.

What is claimed is:

1. A method for generating an alarm during the monitoring of a patient, the method comprising the steps of:
  determining a minute volume of the patient;
  setting at least one of a minute volume lower limit and a minute volume upper limit;
  determining a cumulated volume with an increment function when the measured value drops below the minute volume lower limit or exceeds the minute volume upper limit;
  triggering an alarm when the cumulated volume exceeds a maximum allowable volume;
  storing and reducing the value of the cumulated volume step by step by a defined value by means of a decrement function before the maximum allowable volume is reached and after the minute volume lower limit is exceeded or after the measured value drops again below the minute volume upper limit.

2. A method in accordance with claim 1, wherein:
  the maximum allowable volume is set as a product of a defined time and one of the set minute volume lower limit and the set minute volume upper limit.

3. A method in accordance with claim 2, wherein the product concerning the maximum allowable volume is multiplied by an adjusting factor.

4. A method in accordance with claim 1, wherein triggering an alarm further comprises one of:
  setting at least one of a lower minute volume alarm limit and an upper minute volume alarm limit, which are above the minute volume upper limit and below the minute volume lower limit; and
  triggering the alarm when the measured value drops below the lower minute volume alarm limit or exceeds the upper minute volume alarm limit, independently of the state of the maximum allowable volume being exceeded.

5. A method in accordance with claim 1, wherein the currently cumulated volume is represented by means of a user interface in relation to the maximum allowable volume.

6. A method in accordance with claim 5, wherein at least one of:
  at least one of a visual indication is generated by the user interface when the measured value drops below the minute volume lower limit or exceeds the minute volume upper limit; and
  at least one of a visual and acoustic alarm is triggered when the maximum allowable volume is exceeded.

7. A device for reducing clinically irrelevant alarms during the monitoring of a patient, the device comprising:
  a determination unit determining a minute volume of the patient;
  a setting unit setting at least one of a minute volume lower limit and a minute volume upper limit;
  a comparison unit determining an amount the measured value drops below the minute volume lower limit or exceeds the minute volume upper limit and cumulating at least the amount the measured value drops below the minute volume lower limit as a cumulated volume by means of an increment function; and
  an alarm unit triggering an alarm when the cumulated volume exceeds a maximum allowable volume;
  a user interface, by which the currently cumulated volume can be displayed in relation to the maximum allowable volume.

8. A method for generating an alarm during the monitoring of a patient, the method comprising the steps of:
  determining a minute volume of the patient;
  setting at least one of a minute volume lower limit and a minute volume upper limit;
  determining a cumulated volume with an increment function when the measured value drops below the minute volume lower limit or exceeds the minute volume upper limit;
  triggering an alarm when the cumulated volume exceeds a maximum allowable volume, the maximum allowable volume being set as a product of a defined time and one of the set minute volume lower limit and the set minute volume upper limit;
  multiplying the product concerning the maximum allowable volume by an adjusting factor.

9. A method for generating an alarm during the monitoring of a patient, the method comprising the steps of:
  determining a minute volume of the patient;
  setting at least one of a minute volume lower limit and a minute volume upper limit;
  determining a cumulated volume with an increment function when the measured value drops below the minute volume lower limit or exceeds the minute volume upper limit;

triggering an alarm when the cumulated volume exceeds a maximum allowable volume;

representing the currently cumulated volume by a user interface in relation to the maximum allowable volume.

10. A method for generating an alarm during the monitoring of a patient, the method comprising the steps of:

determining a minute volume of the patient;

setting at least one of a minute volume lower limit and a minute volume upper limit;

calculating a cumulated volume based on an amount the minute volume exceeds said one limit multiplied by a length of time the minute volume exceeds said one limit;

generating an alarm when said cumulated volume exceeds a maximum allowable volume;

reducing said cumulated volume when said minute volume is within said one limit.

11. A method in accordance with claim 10, wherein:

said reducing is performed by a defined value based on an amount the minute volume is within said one limit multiplied by a length of time the minute volume is within said one limit.

\* \* \* \* \*